United States Patent [19]

Lazzari et al.

[11] Patent Number: 5,049,579
[45] Date of Patent: Sep. 17, 1991

[54] SITE SPECIFIC ALKYLATING AGENTS

[75] Inventors: Ettore Lazzari, Milan; Federico Arcamone, Nerviano; Sergio Penco, Milan; Maria A. Verini, Milan; Nicola Mongelli, Milan, all of Italy

[73] Assignee: Farmitalia Carlo Erba, S.r.l., Milan, Italy

[21] Appl. No.: 607,339

[22] Filed: Oct. 31, 1990

Related U.S. Application Data

[60] Division of Ser. No. 485,847, Feb. 21, 1990, Pat. No. 5,017,599, which is a continuation of Ser. No. 336,603, Apr. 7, 1989, abandoned, which is a continuation of Ser. No. 49,987, May 15, 1987, abandoned.

[30] Foreign Application Priority Data

May 20, 1986 [GB] United Kingdom ............... 8612218

[51] Int. Cl.$^5$ ............. A61K 31/40; C07D 403/12
[52] U.S. Cl. .................... 514/422; 548/518
[58] Field of Search .................. 548/518; 514/422

[56] References Cited

U.S. PATENT DOCUMENTS 4,738,980  4/1988  Arcamone et al. ................ 514/422

FOREIGN PATENT DOCUMENTS

| 1421245 | 11/1965 | France . |
| 1004974 | 3/1964 | United Kingdom . |
| 1009797 | 8/1964 | United Kingdom . |
| 1061639 | 7/1965 | United Kingdom . |

OTHER PUBLICATIONS

Arcamone, F., "On Distamycin and Related Compounds, Selective Antiviral Agents" Med. Chem. 1972, pp. 29–45.
Arcamone, F. et al., "Structure and Synthesis of Distamycin A" Nature, Sep. 5, 1964 vol. 203, pp. 1064–1065.
Arcamone, F. et al., Gazzetta Chimica Italiana, vol. 97, pp. 1097–1109. (1967).
Arcamone F. et al., Gazzetta Chimica Italiana, vol. XCIX 1969, pp. 632–640.
Bialer, M. et al., "Structure-Activity Relationship ..."
Jour. of Med. Chem., 1979, vol. 22, No. 11, pp. 1296–1301.
Chandra, P. et al., "Some Structural Requirements for the Antibiotic ... " FEBS Letters, vol. 16, No. 4, Sep., 1971, pp. 249–252.

*Primary Examiner*—Mary C. Lee
*Assistant Examiner*—Peter Davis
*Attorney, Agent, or Firm*—Armstrong, Nikaido, Marmelstein, Kubovcik & Murray

[57] ABSTRACT

The invention relates to distamycin A analogs of the following formula

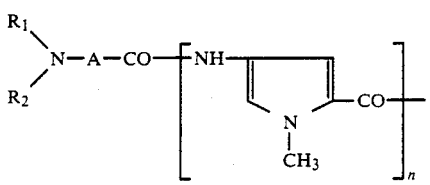

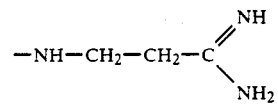

wherein n is 2, 3 or 4; A is an optionally substituted divalent radical chosen from

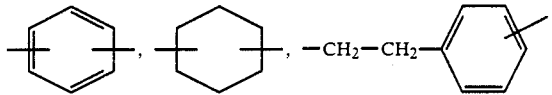

and -Het- wherein Het is a pentatomic or hexatomic heteromonocyclic ring, except pyrrole; and wherein either one of $R_1$ and $R_2$ is hydrogen and the other is an acylating moiety or $R_1$ and $R_2$ are both hydrogen or both alkyl groups optionally substituted, including the pharmaceutically acceptable salts of the said compounds.

The compounds of the invention can be useful antitumor and antiviral agents.

8 Claims, No Drawings

SITE SPECIFIC ALKYLATING AGENTS

This is a division, of application Ser. No. 485,847 filed Feb. 21, 1990, now U.S. Pat. No. 5,017,599, which is a continuation of Ser. No. 336,603 filed Apr. 7, 1989, which is a continuation of Ser. No. 049,987 filed May 15, 1987 (abandoned).

The present invention refers to new antitumor alkylating and antiviral agents related to the known antibiotic distamycin A,

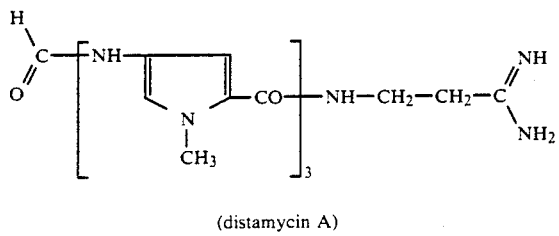

(distamycin A)

which belongs to the family of the pyrroleamidine antibiotics and is reported to interact reversibly and selectively with DNA-AT sequences interfering with both replication and transcription [Nature 203, i064 (i064); FEBS Letters 7 (1970) 90; Prog. Nucleic Acids Res.-Mol.Biol , 15, 285 (1975)].

The present invention relates to new distamycin A analogs in which the distamycin formyl group is substituted by aromatic, alicyclic or heterocyclic moieties bearing alkylating groups, to a process for their preparation, to pharmaceutical compositions containing them and to the use of said compounds and compositions as antitumor and antiviral agents. The invention herein provides compounds of the general formula (I)

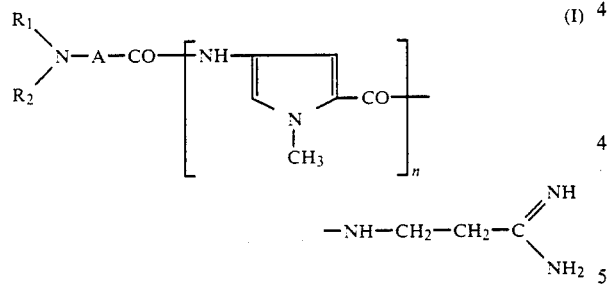

wherein
n is 2, 3 or 4;
A is a divalent radical chosen from

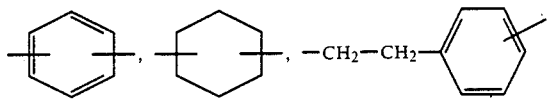

and -Het-, wherein Het is a pentatomic or hexatomic heteromonocyclic ring, except pyrrole, the said radical being unsubstituted or substituted by one or more substituents chosen from $C_1$-$C_6$ alkyl, $C_1$-$C_6$ alkoxy, cyano and trifluoromethyl; and either one of $R_1$ and $R_2$ is hydrogen and the other is a) a group

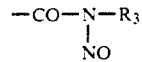

in which $R_3$ is $C_1$-$C_6$ alkyl unsubstituted or substituted by halogen atoms; phenyl; or cyclohexyl; or b) a group —CO—$(CH_2)_m$—$R_4$ in which m is zero, 1, 2 or S and $R_4$ is hydrogen, halogen, hydroxy, aziridinyl or oxiranyl; or $R_1$ and $R_2$ are the same and they are both hydrogen or both a $C_1$-$C_6$ alkyl group unsubstituted or substituted by halogen, hydroxy or $C_1$-$C_6$ alkoxy.

The invention includes also the pharmaceutically acceptable salts of the compounds of formula (I) as well as all the possible isomers covered by the formula (I), both separately and in mixture.

The alkyl groups and the aliphatic moieties of the alkoxy groups may be branched or straight chain.

A $C_1$-$C_6$ alkyl group is, preferably, $C_1$-$C_4$ alkyl, in particular, e.g., methyl, ethyl, n-propyl, iso-propyl, n-butyl and tert.butyl.

A $C_1$-$C_6$ alkoxy is preferably, $C_1$-$C_4$ alkoxy, in particular, for instance, methoxy, ethoxy, n-propoxy or tert.butoxy. A halogen atom is, preferably, chlorine, bromine or fluorine. When A represents a heteromonocyclic ring as defined above, it is, preferably a pentatomic or hexatomic saturated or unsaturated, most preferably unsaturated, heteromonocyclic ring containing at least one, preferably one or two, heteroatom chosen from O, S and N.

Examples of said heteromonocyclics are thiophene, thiazole, pyridine, isoxazole, furane, triazole and imidazole. Preferably these rings are either unsubstituted or substituted by $C_1$-$C_6$ alkyl, in particular methyl; 1-methyl-imidazole is an example of substituted heteromonocyclic.

Pharmaceutically acceptable salts of the compounds of formula (I) are their salts with pharmaceutically acceptable, either inorganic or organic, acids.

Examples of inorganic acids are hydrochloric, hydrobromic, sulfuric and nitric acid; examples of organic acids are acetic, propionic, succinic, malonic, citric, tartaric, methanesulfonic and p-toluenesulfonic acid. A particularly preferred n value is 3. Particularly preferred A values are

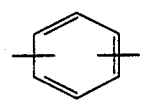

and -Het- wherein Het is as defined above, especially one of the specific heteromonocyclics indicated before, in particular, for instance. thiophene, thiazole and i-methyl-imidazole, thiophene, thiazole and 1-methyl-imidazole. Particularly preferred values for the group

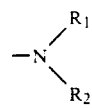

are either
(a')

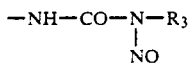

wherein $R_3$ is unsubstitute or halo-substituted $C_1$–$C_6$ alkyl, for example methyl, ethyl or, respectively, 2-chloroethyl, or (bb′) —NH—CO—$(CH_2l)_m$—$R_4$ wherein m is zero. 1, 2 or 3, especially zero, and $R_4$ is aziridinyl or oxiranyl; or (cc′)

wherein $R'_1$ and $R'_2$ are the same and are each a halo-substituted $C_1$–$C_6$ alkyl, 2-chloroethyl for example. A particularly preferred class of compounds of the invention are the compounds of formula (I) wherein n is 3; A is a divalent radical chosen from

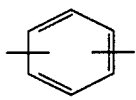

and the group -Het- wherein -Het- is a pentatomic or hexatomic heteromonocyclic ring, except pyrrole, containing one or two heteroatoms chosen from O, S and N, either unsubstituted or substituted by $C_1$–$C_6$ alkyl; and the group

is either (i)

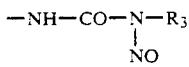

wherein $R_3$ is unsubstituted or halo-substituted $C_1$–$C_6$ alkyl, or (ii)

wherein $R'_1$ and $R'_2$ are the same and are each a halo-substituted $C_1$–$C_6$ alkyl, and the pharmaceutically acceptable salts thereof.

In the above preferred class, preferred Het values are thiophene, thiazole, pyridine, isoxazole, furane, triazole, imidazole and 1-methyl-imidazole, particularly thiophene, thiazole and 1-methyl-imidazole; when $R_3$ is unsubstituted $C_1$–$C_6$ alkyl, methyl and ethyl are preferred, especially methyl; when $R_3$ and/or $R'_1$ and $R'_2$ are a halo .substituted $C_1$–$C_6$ alkyl, this is, preferably, 2-chloroethyl.

Examples of specific compounds under this invention, especially in the form of salts with hydrochloric acid, are the following:

β-[1-methyl-4-[1-methyl-4-[1-methyl-4-(N′-methyl-N′-nitrosoureido-benzene) -1-carboxamido]pyrrole-2-carboxamido]pyrrole-2-carboxamido]pyrrole-2-carboxamido]propionamidine;

β1-methyl-4-[1-methyl-4-[1-methyl-4-L4-N′-(2-chloroethyl)-N′-nitrosoureido-benzene)-1-carboxamido- pyrrole-2-carboxamido]pyrrole-2-carboxamido]pyrrole-2-carboxamido]propionamidine;

β[1-methyl-4-[1-methyl-4-[1-methyl-4-[4-N,N-bis(2-chloroethyl) aminothiophen-2-carboxamido]pyrrole-2-carboxamido]pyrrole-2-carboxamido]pyrrole-2-carboxamido]propionamidine;

β[1-methyl-4-[1-methyl-4-[4-N,N-bis(2-chloroethyl) amino-benzene-1-carboxamido]pyrrole-2-carboxamido]pyrrole-2-carboxamido]pyrrole-2-carboxamido]-propionamidine, and β-[1-methyl-4-[1-methyl-4-[1-methyl-4-[3-N,N-bis(2-chloroethyl) amino-benzene-1-carboxamido-pyrrole-2-carboxamido]pyrrole-2-carboxamido]pyrrole-2-carboxamido]propionamidine. The compounds of the invention are prepared by a process comprising reacting a compound of formula (II)

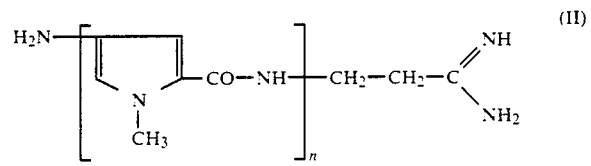

wherein n is as defined above, with a compound of formula (III)

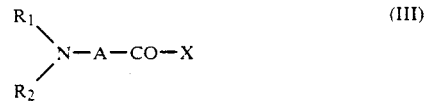

wherein $R_1$, $R_2$ and A are as defined above and X is hydroxy or a leaving group and, if desired, salifying a compound of formula (I) or obtaining a free compound from a salt, and/or, desired, separating a mixture of isomers of formula (I) into the single isomers.

The leaving group X in the compounds (III) may be, for example, halogen, chlorine in particular, or another displaceable group such as, for instance, 2,4,5-trichlorophenoxy, 2,4-dinitrophenoxy, succinimido-N-oxy or imidazolyl. The reaction between a compound of formula (II) and a compound of formula (III) wherein X is —OH is preferably carried out in a molecular ratio from 1:1 to 1:2 in an organic solvent such as, e.g., dimethylsulphoxide, hexamethylphosphotriamide, dimethylacetamide, dimethylformamide, ethyl alcohol, benzene or pyridine, in the presence of an organic or inorganic base such as, e.g., triethylamine, diisopropyl ethylamine or sodium carbonate or bicarbonate, and of a condensing agent such as, e.g., N-ethyl-N′-(S-dimethylaminopropyl)carbodiimide or, preferably, N,N′-dicyclohexylcarbodiimide. The reaction temperature may vary from about −10° C. to about 50° C. and the reaction time from about 1 to about 24 hours.

The reaction between a compound of formula (II) and a compound of formula (III), wherein X is halogen or another leaving group, e.g., 2,4,5-trichlorophenoxy or succinimido-N-oxy or imidazolyl, may be carried out in analogous conditions but without the condensing agent.

For the reaction between a compound of formula (II) and a compound of formula (III) wherein one of $R_1$ and $R_2$ is hydrogen and the other is a group

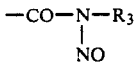

as defined above under a), and X is —OH, preferred solvents are, e.g., dimethylsulphoxide, hexamethylphosphotriamide, dimethylacetamide or, preferably, dimethylformamide; preferred bases are organic bases such as, e.g., triethylamine or diisopropyl ethylamine; and preferred reaction times are from about 1 to about 12 hours. For the reaction between a compound of formula (II) and a compound of formula (III), wherein one of $R_1$ and $R_2$ is hydrogen and the other is a group

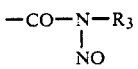

as defined above under a), and X is a halogen atom or another leaving group, e.g., 2,4,5-trichlorophenoxy or succinimido-N-oxy or imidazolyl, preferred solvents are, e.g., dimethylformamide or pyridine; preferred bases are organic bases, e.g. diisopropylethylamine; preferred temperatures are from about 0° C. to about 25° C. and preferred reaction times are from about two hours to about ten hours.

For the reaction between a compound of formula (II) and a compound of formula (III) wherein one of $R_1$ and $R_2$ is hydrogen and the other is a group —CO—(CH$_2$)$_m$—R$_4$ as defined above under b), X being either —OH or halogen or another leaving group, preferred solvents are, e.g., dimethylsulphoxide, hexamethylphosphotriamide, dimethylacetamide or, preferably, dimethylformamide; preferred bases are organic bases such as, e.g, triethylamine or diisopropyl ethylamine; and preferred reaction times are from about 2 to about 24 hours. For the reaction between a compound of formula (II) and a compound of formula (III) wherein $R_1$ and $R_2$ are the same and are both hydrogen or both a $C_1$-$C_6$ alkyl group unsubstituted or substituted by halogen, hydroxy or $C_1$-$C_6$ alkoxy, and X is halogen or another leaving group, preferred bases are both organic and inorganic bases such as, e.g., triethylamine or diisopropyl ethylamine or sodium carbonate or bicarbonate; preferred solvents are, for instance, ethyl alcohol, benzene, dimethylformamide, pyridine, dimethylacetamide, hexamethylphosphotriamide; preferred temperature is the room temperature and preferred reaction time is around 18 hours. Analogous conditions, though with the additional presence of a condensing agent, are the preferred ones also for the reaction between a compound (II) and a corresponding compound (III) wherein X is -OH: dicyclohexylcarbodiimide is a preferred condensing agent and dimethylformamide is a preferred solvent.

The compounds of formula (II) are known compounds or may be prepared by known methods from known compounds: see, for instance, Arcamone et al. Gazzetta Chim.Ital. 97, 1097 (1967). The compounds of formula (III) are known compounds too or may be prepared from known compounds through reactions well described in the organic chemistry: see for example J.Med. Chem. 9, 882 (1900) and 25, 178 (1982).

The salification of a compound of formula (I) as well as the preparation of a free compound from a salt may be carried out by known standard methods.

Well known procedures such as, e.g. fractional crystallization or chromatography may also be followed for separating a mixture of isomers of formula (I) into the single isomers.

The new compounds of formula (I) prepared according to the above described procedures may be as well purified by conventional methods such as, e.g., silica gel or alumina column chromatography, and/or by recrystallization from an organic solvent such as, e.g., a lower aliphatic alcohol, e.g. methyl, ethyl or isopropyl alcohol, or dimethylformamide.

The compounds of the invention can be useful as antineoplastic and antiviral agents. They show, in particular, cytostatic properties towards tumor cells so that they can be useful, e.g., to inhibit the growth of various tumors, such as, for instance, carcinomas, e.g. mammary carcinoma, lung carcinoma, bladder carcinoma, colon carcinoma, ovary and endometrial tumors Other neoplasias in which the compounds of the invention could find application are, for instance, sarcomas, e.g. soft tissue and bone sarcomas, and the hematological malignancies such as, e.g. leukemias. The following table reports in vitro antitumor activity data referring to the compounds of the invention β-[1-methyl-4-[1-methyl-4-[1-methyl-4-[4-N,N-bis(2-chloro-ethyl) aminobenzene-1-carboxamido-pyrrole-2-carboxamido]pyrrole-2-carboxamido]pyrrole-2-carboxamido]propionamidine hydrochloride (internal code FCE 24517) and β-[1-methyl-4-[1-methyl-4-[1-methyl -4-[4-N,N-bis(2-chloroethyl)aminothiophen-2-carboxamido]pyrrole-2-carboxamido]pyrrole-2-carboxamido]pyrrole-2-carboxamido]-propionamidine hydrochloride (internal code FCE 24690), in comparison with distamycin A, which is deemed to be the closest, and the most widely known and studied, reference compound.

The in vitro antitumor activity was evaluated by cytotoxicity studies carried out on murine L1210 leukemia cells, L-PAM resistant leukemia cells and P388 leukemia cells, as well as on HeLa cells. Cells were derived from in vivo tumors and established in cell culture. Cells were used until the tenth passage. Cytotoxicity was determined by counting surviving cells after 4 hours treatment and 4B hours growth in drug-free medium. For HeLa cells the colony inhibition test according to Cancer Chemother. Pharmacol. 1:249–254, 1978, was used. The percentage of cell growth in the treated cultures was compared with that of controls. ID$_{50}$ values (doses inhibiting 50% of the cellular growth in respect to controls) were calculated on dose-response curves.

TABLE

| Compound | ID$_{50}$ (μg/ml) | | | |
|---|---|---|---|---|
| | L1210[1] | L1210/LPAM[1] | P388[2] | HeLa[3] |
| distamycin A | 198 | 136 | 25 | 3.9 |
| FCE 24517 | 0.985 | 0.430 | 0.21 | 0.014 |
| FCE 24690 | 1.365 | 0.985 | 0.22 | 0.037 |

[1]Cytotoxicity evaluated after 4 hours treatment;
[2]Cytotoxicity evaluated after 48 hours treatment;
[3]Colony inhibition test carried out after 24 hours treatment.

The compounds of the invention show also a remarkable effectiveness in interfering with the reproductive activity of the pathogenic viruses and protect tissue cells from viral infections.

For example they show activity against DNA viruses such as, for instance, herpes, e.g. herpes simplex and herpes zoster, viruses, virus vaccinia, RNA viruses such as, e.g. Rhinovirus and Adenoviruses, and against retroviruses such as, for instance, Sarcoma viruses, e.g., Murine sarcoma virus, and Leukemia viruses, e.g. Friend leukemia virus. Thus, for example, herpes, coxsackie and respiratory syncytial viruses were tested in fluid medium as follows. Serial twofold dilutions of the compounds from 200 to 1.5 mcg/ml were distributed in duplicate 0.1 ml/well in 96 wells microplates for tissue culture.

Cell suspensions ($2'10^5$ cells/ml) infected with about $5 \times 10^{-3}$ $TCID_{50}$ of virus/cell were immediately added 0.1 ml/well. After 3–5 day incubation at 37° C. in $CO_2 5\%$, the cell cultures were evaluated by microscopical observation and Minimum Inhibiting Concentration (MIC) were determined, MIC being the minimum concentration which determines a reduction of cytopathic effect in comparison with the infected controls.

The compounds of the invention can be administered by the usual routes, for example, parenterally, e.g. by intravenous injection or infusion, intramuscularly, subcutaneously, topically or orally.

The dosage depends on the age, weight and conditions of the patient and on the administration route.

For example, a suitable dosage for administration to adult humans may range from about 0.1 to about 200–250 mg pro dose 1–4 times a day.

As already said, the pharmaceutical compositions of the invention contain a compound of formula (I) as the active substance, in association with one or more pharmaceutically acceptable excipients.

The pharmaceutical compositions of the invention are usually prepared following conventional methods and are administered in a pharmaceutically suitable form.

For instance, solutions for intravenous injection of infusion may contain as carrier, for example, sterile water or, preferably, they may be in the form of sterile aqueous isotonic saline solutions.

Suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

Furthermore, according to the invention there is provided a method of treating tumors and viral infections in a patient in need of it, comprising administering to the said patient a composition of the invention. The following examples illustrate but do not limit the invention.

The abbreviations DMF and DMSO stand for dimethylformamide and, respectively, dimethylsulfoxide.

EXAMPLE 1

β-[1-methyl-4-[1-methyl-4-[1-methyl-4-[4-(N'-methyl-N'-nitrosoureidobenzene)-1-carboxamido]pyrrole-2-carboxamido]pyrrole-2-carboxamido]pyrrole-2-carboxamido]propionamidine, hydrochloride.

A solution of 0.1 ml of triethylamine in 1 ml of DMF was added in 5' to a stirred solution of 0.41g of N-deformyl distamycin in 2.5 ml of DMF at room temperature and under nitrogen. After 15' 0.17 g of 4-(N-nitroso-N-(methylureido)benzoic acid and 0.16 g of dicyclohexylcarbodiimide were added in small portions. The reaction mixture was stirred two hours and 25 ml of ethyl ether were added. The solid collected by filtration was purified by chromatography on silica gel with mixtures of ethylacetate, methanol and acetic acid, yielding 0.175 g of the title compound, m.p. 205°–210° C. (dec.) (from isopropanol).

FD-MS: m/z 572 [6, $(M-C_2H_2N_2O_2)^+$·]; 555 [7.5, $(M-NH_3-C_2H_2N_2O_2)^+$·]; 502 (100);

PMR (DMSO-$d_6$) δ:

10.90 (broad signal, 1H)

10.31 (s, 1H)

9.99, 9.92 (s, 2H)

8.97, 8.63 (broad signal, 4H)

8.22 (t, J=5.5Hz, 1H)

7.97, 7.86 (two doublets, J=8.8Hz, 4H)

7.32, 7.24, 7.18, 7.11, 7.06, 6.94 (broad signal, 6H)

3.86, 3.83, 3.80 (s; 9H)

3.48 (m, 2H)

3.17 (s, 3H)

2.60 (m, 2H).

By analogous procedure it can be also prepared the corresponding N'-(2-chloro-ethyl)-N'-nitrosoureido benzoyl derivative of N-deformyldistamycin, i.e. the compound B-1-methyl-4-[1-methyl-4-[-1-methyl-4-4--(N'-(2-chloro-ethyl-N'-nitrosoureido-benzene)-1-carboxamido]pyrrole-2-carboxamido]pyrrole-2-carboxamido]pyrrole-2-carboxamido]propionamidine, hydrochloride, m.p. 182° C. (dec.),

MS-FD : M+(707);M+-17 (690); M+-70 (637)

PMR (DMSO-$d_6$) δ:

2.39 (t,2H)

3.50 (dt,2H)

3.69 (t,2H)

3.79 (s,3H)

3.85 (s,3H)

3.89 (s,3H)

4.19 (t,2H)

6.89–7.25 (m,8H) .

7.88 (m,2H)

9.01 (b,4H)

9.92 (s,1H)

9.94 (s,1H)

10.06 (s,1H)

| UV (EtOH 95%; C = 0.00172%): | $\lambda_{max}$ | $\epsilon$ |
|---|---|---|
| | 240 | 30,294 |
| | 310 | 41,587 |

EXAMPLE 2

β-[1-methyl-4-[1-methyl-4-[1-methyl-4-(4-N,N-bis(2-chloroethyl)aminothiophen-2-carboxamido]pyrrole-2-carboxamido]pyrrole-2-carboxamido]pyrrole-2-carboxamido]propionamidine, hydrochloride

Step one

The intermediate 4-[N,N-bis-(2-chloroethyl)]aminothiophen-2-carboxylic acid.

Starting from 1.7a g of methyl-4-nitrothiophen-2-carboxylate by reduction with zinc in methanol solution saturated with hydrogen chloride [according to Can. J. Chem. 44, 2888 (1966) for the reduction of the 5-nitrothiophen derivative] 0.90 b of methyl-4-aminothiophen-2-carboxylate were obtained, m.p. 81°–82° C. (from diisopropylether).

4 g of cold ethylene oxide were introduced to a solution of 0.9 g of methyl-4-aminothiophen-2-carboxylate in 12.5 ml of 40% aqueous acetic acid at 5° under stirring. The mixture maintained overnight at room temperature in a sealed flask was concentrated to small volume and then diluted with 25 ml of water. Solid sodium bicarbonate was added and the mixture was extracted with ethyl acetate.

By evaporation of the organic solvent 1.3 g of methyl-4-[N,N-bis-(2-hydroxyethyl)]-aminothiophen-2-carboxylate were obtained as a light brown oil which solidifies on standing, m.p. 68°–60° C. (from ethylacetate-hexane 60/40).

The bis-hydroxyethylamino derivative obtained (1.3 g) was dissolved in 1.96 ml of phosphorus oxychloride and the mixture was refluxed 45 minutes. After evaporation under vacuum the dark residue was treated with 7.75 ml of concentrated hydrochloric acid at 100° for three hours. The mixture was cooled, 21 ml of cold water were added and the resulting solution was extracted with ethyl acetate. Evaporation of the organic solvent and purification of the solid residue by chromatography on a silica gel column eluting with a mixture of ethyl acetate-methanol afforded 0.49 g of 4-[N,N-bis-(2-chloroethyl)]-aminothiophen-2-carboxylic acid, m.p. 135°–137° C. (from benzene-hexane 60/40);

EI/MS: m/z 267 (11,M+);218 (100); 63 (57);
PMR (CDCl$_3$) δ:
9.50 (broad signal, 1H)
7.45 (d, J=2.3Hz, 1H)
6.30 (d, J=2.3Hz, 1H)
3.63 (s, 8H)

Step two

The title compound

A solution of 0.1 ml of triethylamine in 0.5 ml of DMF was added to a solution of 0.45 g of deformyl distamycin dihydrochloride in 4.5 ml of DMF at room temperature and under nitrogen. The mixture was treated with 0.23 g of 4-[N,N-bis-(2-chloroethyl)]-aminothiophen-2-carboxylic acid and 0.7? g of dicyclohexylcarbodiimide in small portions. The resulting mixture was stirred overnight, then filtered and evaporated to dryness under vacuum. The solid residue was purified by chromatography on silica gel column eluting with mixtures of ethyl acetate and ethanol (9:1 and 8:2 by volume). 0.22 g of the title compound were obtained, m.p. 199°–204° C. (after recrystallization from isopropyl alcohol); FD-MS: m/z 703MH+; PMR (DMSO-d$_6$) δ:
10.28 (broad signal, 1H)
9.94, 9.98 (s, 2H)
8.9–9.3 (broad signal, 4H)
8.24 (t, J=5.5Hz, 1H)
7.67, 6.44 (two doublets, J=1.6Hz, 2H)
7.24, 7.18, 7.07, 7.04, 6.92 (d, J=1.8Hz, 6H)
3.85, 3.83, 3.79 (s, 9H)
3.8–3.6 (m, 8H)
3.47 (m, 2H)
2.57 (m, 2H).

By analogous procedure the following compounds can be prepared: β-[1-methyl-4-1-methyl-4--1-methyl-4-4-[N,N-bis(2-chloroethyl)]-aminoimidazole-1-methyl-2-carboxamido-pyrrole-2-carboxamido]pyrrole-2-carboxamido-pyrrole-2-carboxamido]-propionamidine hydrochloride;

β-[1-methyl-4-[1-methyl-4-[1-methyl-4--5-N--N-bis-(2-chloroethyl)]-aminoimidazole-1-methyl-2-carboxamido]pyrrole-2-carboxamido]pyrrole-2-carboxamido]-2-carboxamido]propionamidine hydrochloride;

β-[1-methyl-4-1-methyl-4-L-1-,methyl,N-bis(2-chloroethyl) aminothiazole-2-carboxamido-pyrrole-2-carboxamido]pyrrole-2-carboxamido]pyrrole-2-carboxamido-]propionamidine hydrochloride; β-[1-methyl-4-[1-methyl-4-[? -methyl-4--5-[N,N-bis(2-chloroethyl) aminothiazole-2-carboxamido ™ pyrrole-2-carboxamido-pyrrole-2-carboxamido-pyrrole-2-carboxamido-propionamidine hydrocloride.

EXAMPLE 3

β-[1-methyl-4-[1-methyl-4-1-methyl-4-(4-N,N-bis(2-chloroethylamino benzene-1-carboxamido]pyrrole-2-carboxamido]pyrrole-2-carboxamido]pyrrole-2-carboxamido]propionamidine, hydrochloride A solution of 0.195 g of sodium bicarbonate in 3 ml of water was added to a cooled solution of 0.4 g of deformyl distamycin in 21 ml of ethanol. To this mixture a solution of 0.32 g of 4-N,N-(2-chloroethyl)aminobenzoyl chloride in 3 ml of benzene was added dropwise. The mixture was stirred three hours at 5° and then twelve hours at room temperature. Evaporation under vacuum gave a solid residue which was chromatographed on silica gel column eluting with mixtures of chloroform-methanol (G:1 and 7:3 by volume) yielding 0.22 g of the title compound, m.p.2G5° C dec. (from isopropyl alcohol and ethyl ether; FD-MS: m/z 697 (34, MH+); 679 (100, M-NH$_3$); PMR (DMSO-d$_6$) δ:
T=50° C.
9.91 (s, 1H)
9.82, 9.79 (s, 2H)
8.94, 8.61 (broad signal, 4H)
8.11 (t, J=5.5Hz, 1H)
7.85, 6.82 (two doublets, J=8.9Hz, 4H)
7.26, 7.20, 7.15, 7.07, 7.05, 6.94 (d, J=1.6Hz, 6H)
3.85, 3.84, 3.81 (s; 9H)
3.78 (s, 8H)
3.51 (m, 2H)
2.64 (t, J=6.6Hz, 2H).

By analogous procedure the following compounds can be obtained:

β-[1-methyl-4-[1-methyl-4-[1-methyl-4-[3-N,N-bis(2-chloroethyl) amino-benzene-1-carboxamido pyrrole-2- carboxamid]pyrrole-2-carboxamido-.pyrrole-2-carbox-amido-propionanidine hydrochloride, m.p. 170° C. (dec.);

MS-FD: M+-17 (679); M+-70 (626l); M+-2 (CH₂CH₂Cl) (571);

PMR (DMSO-d₆) δ:
2.63 (t,3H)
3.35-4.00 (m,19H)
6.80-7.40 (m,10H)
8.20 (t,1H)
8.88 (b,4H)
9.90 (1.1H)
9.94 (s,1H)
10.15 (s,1H

| UV (EtOH 95%: C = 0.003107%): | $\lambda_{max}$ | $\epsilon$ |
|---|---|---|
| | 235 | 35,896 |
| | 262 | 35,309 |
| | 310 | 39,200; |

β-[1-methyl-4-1-1-methyl-4-1-1-methyl-4-[4-oxiranecarbonylamino -benzene-1-carboxamido]pyrrole-2-carboxamido]pyrrole-2-carboxamido-propionamidine hydrochloride;

β-[1-methyl-4-1--methyl-4-1--methyl-4-S---oxiranecarbonylamino -benzene-1-carboxamido]pyrrole-2-carboxamido-]pyrrole-2-carboxamido]pyrrole-2-carboxamido-]propionamidine hydrochloride;

β-[1-methyl-4-[1-methyl-4-[1-methyl-4-[4-[1-(aziridine) carbonylamino-benzene-1-carboxamidopyrrole-2-carboxamido]pyrrole-2-carboxamidopyrrole-2-carboxamidopropionamidine hydrochloride;

β-[1--methyl-4-1--methyl-4-[1-methyl-4-S----1-(aziridine) carbonylamino-benzene-1-carboxamido]-pyrrole-2-carboxamido]pyrrole-2-carboxamido]pyrrole-2-carboxamido]propionamidine hydrochloride.

EXAMPLE 4

Tablets each weighing 0.250 g and containing 50 mg of the active substance can be manufactured as follows:
Composition (for 10,000 tablets)
β-[1-methyl-4-[-1-methyl-4---1-methyl-4-4-N-'N-bis(2-chloroethyl) amino-benzene-1-carboxamido-pyrrole-2-carboxamido]pyrrole-2-carboxamido-pyrrole-2-carboxamido]propionamidine hydrochloride 500 g
Lactose 1,400 g
Corn starch 500 g
Talc powder 80 g
Magnesium stearate 20 g.

The β-[1-methyl-4-[-1-methyl-4-1-methyl-4-4-N,N-bis(2-chloroethyl) amino-benzene-1-carboxamido]pyrrole-2-carboxamido]pyrrole-2-carboxamido]pyrrole-2-carboxamido]propionamidine hydrochloride, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 5

Capsules, each dosed at 0.200 g and containing 20 mg of the active substance can be prepared as follows:
Composition for 500 capsules:

β-[1-methyl-4-[1-methyl-4-[1-methyl-4-4-N-'N-bis(2-chloroethyl) amino-benzene-1-carboxamido]pyrrole-2-carboxamido]pyrrole-2-carboxamido]pyrrole-2-carboxamido-propionamidine hydrochloride 10 g
Lactose 80 g
Corn starch 5 g
Magnesium stearate 5 g.

This formulation can be encapsulated in two-piece hard gelatin capsules and dosed at 0.200 g for each capsule.

EXAMPLE 6

Intramuscular injection 25 mg/ml

An injectable pharmaceutical composition can be manufactured by dissolving 25 g of B-1--methyl-4--1-methyl-4--1-methyl-4-N,N-bis (2-chloro-ethyl-)aminothiophen-2-carboxamido]-pyrrole-2-carboxamido]pyrrole-2-carboxamido]-pyrrole-2-carboxamido]propionamidine hydrochloride in sterile propyleneglycol (1000 ml) and sealing ampoules of 1-5 ml.

We claim:

1. A compound of formula (I)

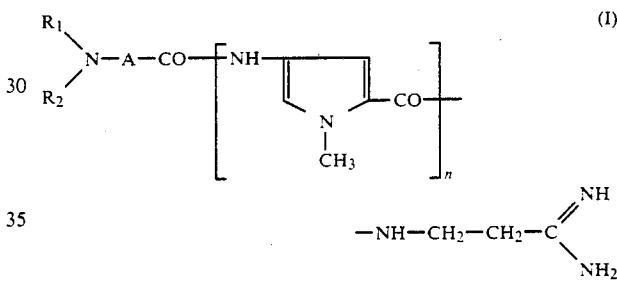

$$-NH-CH_2-CH_2-C\begin{matrix}NH\\ \diagup\\ \diagdown\\ NH_2\end{matrix}$$

wherein
n is 2, 3 or 4;
A is a divalent thiophene said radical being unsubstituted or substituted by one or more substituents chosen from $C_1$-$C_6$ alkyl, $C_1$-$C_6$ alkoxy, provided, however, that when $R_1$ and $R_2$ are both chloroethyl, and A is

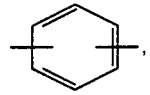

then n is 2 or 4 cyano and trifluoromethyl; and either one of $R_1$ and $R_2$ is hydrogen and the other is
a) a group

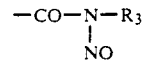

in which $R_3$ is $C_1$-$C_6$ alkyl unsubstituted or substituted by halogen atoms; phenyl; or cyclohexyl; or
b) a group —CO—(CH₂)$_m$—R₄ in which m is zero, 1, 2 or 3 and R₄ is hydrogen, halogen, hydroxy, aziridinyl or oxiranyl; or $R_1$ and $R_2$ are the same and they are both hydrogen or both a $C_1$-$C_6$ alkyl group unsubstituted or substituted by halogen, hydroxy or $C_1$-$C_6$ alkoxy, and the pharmaceutically acceptable salts thereof.

2. A compound having the formula (I) reported in claim 1 wherein n is 3; A is either unsubstituted or substituted by $C_1$-$C_6$ alkyl; and the group

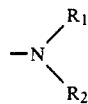

is either (i)

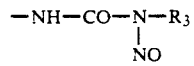

wherein $R_3$ is unsubstituted or halo-substituted $C_1$-$C_6$ alkyl, or (ii)

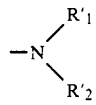

wherein $R'_1$ and $R'_2$ are the same and are each a halo-substituted $C_1$-$C_6$ alkyl, and the pharmaceutically acceptable salts thereof.

3. The compound β-[1-methyl-4-[1-methyl-4-[1-methyl-4-[4-N,N-bis(2l-chloroethyl) aminothiophen-2-carboxamido]pyrrole-2-carboxamido]pyrrole-2-carboxamido]pyrrole2-carboxamido]propionamidine.

4. A pharmaceutical composition containing a suitable carrier and/or diluent and, as an active principle, an effective amount of the compound according to claim 3 or a pharmaceutically acceptable salt thereof.

5. A method of producing antitumor effect in a patient in need of it, said method comprising administering an effective amount of the compound of claim 3.

6. A method of producing antitumor effect in a patient in need of it, said method comprising administering an effective amount of a pharmaceutical composition of claim 4.

7. A method of producing antiviral effect in a patient in need of it, said method comprising administering an effective amount of the compound of claim 3.

8. A method of producing antiviral effect in a patient in need of it, said method comprising administering an effective amount of a pharmaceutical composition of claim 4.

* * * * *